United States Patent [19]

Gritter

[11] 4,171,571
[45] Oct. 23, 1979

[54] DENTAL HANDPIECES

[76] Inventor: Frederik Gritter, 11 Glen Rd., Oatley, N.S.W., Australia

[21] Appl. No.: 757,241

[22] Filed: Jan. 6, 1977

[30] Foreign Application Priority Data

Jan. 8, 1976 [AU] Australia .............................. PC4480

[51] Int. Cl.² .............................................. A61C 1/10
[52] U.S. Cl. .................................... 32/26; 32/DIG. 1; 91/499; 91/482
[58] Field of Search ........................ 32/26, 23, DIG. 1; 415/503; 91/499, 482, 483, 473, 474

[56] References Cited

U.S. PATENT DOCUMENTS

| | | |
|---|---|---|
| 1,913,003 | 6/1933 | Shaff ...................................... 91/499 |
| 3,043,412 | 7/1962 | Bartholomäus et al. .............. 91/499 |
| 3,799,033 | 3/1974 | Pruvot ................................... 91/482 |

FOREIGN PATENT DOCUMENTS 357199 4/1919 Fed. Rep. of Germany .......... 415/503

Primary Examiner—Louis G. Mancene
Assistant Examiner—John J. Wilson
Attorney, Agent, or Firm—Brisebois & Kruger

[57] ABSTRACT

A dental handpiece has a rotor with pistons in longitudinal bores, the pistons being displaced by air pressure and engaging against a swash plate to cause the rotor to rotate. The direction and speed of rotation is controlled by an air distributor member having a plate which controls the amount of and direction of the air flow.

4 Claims, 4 Drawing Figures

DENTAL HANDPIECES

BRIEF DESCRIPTION OF THE INVENTION

The dental handpieces according to the invention comprise an airmotor having a swash plate/piston rotor combination in which the rotor moves and the swash plate is of fixed inclination so that the rotor acts as a flywheel and energy storing device.

The present invention provides a dental handpiece having a cylindrical body, an air distributing member mounted therein and in communication with a manifold, a rotor mounted on a shaft journalled with respect to the body and having a plurality of bores in which pistons are axially slidable in response to air pressure, said pistons engaging the surface of the fixed inclination swash plate in the housing, the air distributing member being angularly displaceable to vary the position of the inlet air with respect to the outlet air for neutral forward or reverse rotation of the rotor and any position therebetween.

The handpiece of the present invention is further characterised by an internal brake member which is released by air pressure in the inlet supply but which engages the rotor when the air pressure ceases.

A further feature of the present invention is that the air distributor member acts as a speed control whereby if it is positioned between the full forward or reverse positions, part of the air supply is bled into the return air line therefore limiting the speed of rotation of the device.

DESCRIPTION OF PREFERRED EMBODIMENT

The invention is hereinafter described with reference to the accompanying drawings in which.

Figure 1:
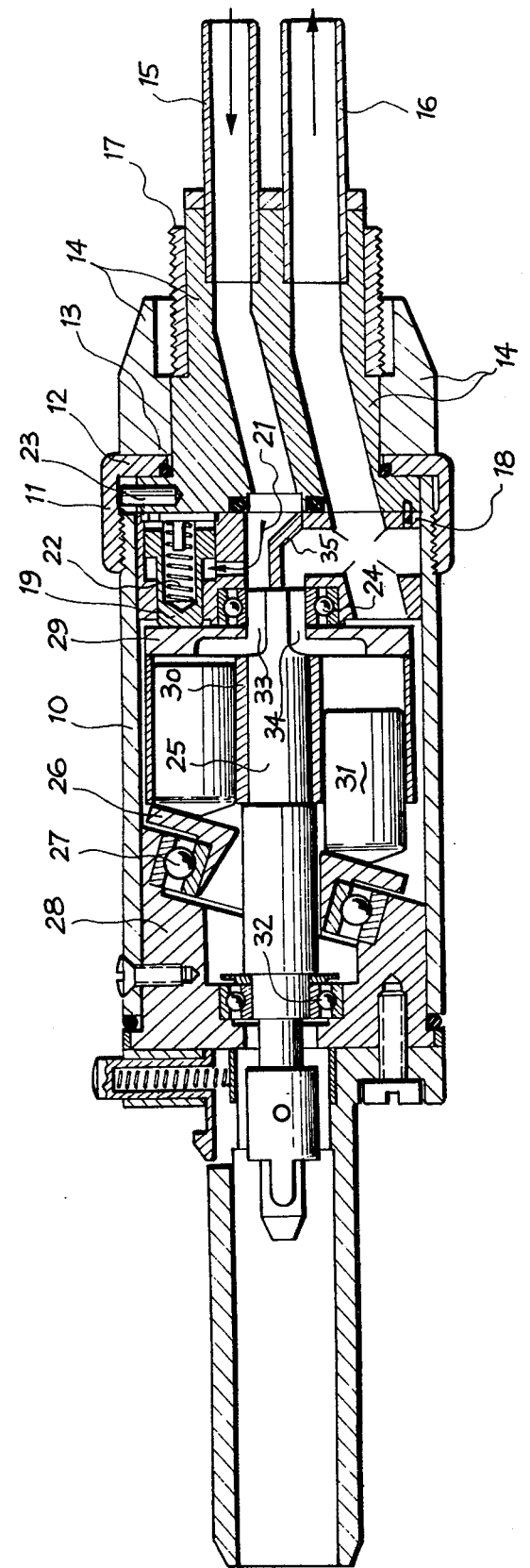
FIG. 1 is a sectional side elevation of the device of this inventional along its longitudinal centre line.

A cylindrical casing 10, (FIG. 1) is provided at its rearward end with an apertured end cap 11, whereby the flange part 12, of the cap 11, extends into a groove 13, in a manifold 14, having air inlet 15, an air outlet 16, and a threaded coupling part 17, as well as a water inlet and water outlet not shown. The water is carried to the front of the handpiece by an external pipe.

The air inlet 15, and outlet 16, pass into a distributor member 18, pinned to the manifold 14, and incorporating a brake cylinder 19, in which a piston 20, slides in response to air pressure at 21, or a return spring 22. The latter causes the piston 20, to engage against a rotor 29 when the air flow ceases. A pin 23, in the member 18, engages in a camtrack in the body 10, to limit the angular movement therebetween for forward and reverse.

Figure 2:
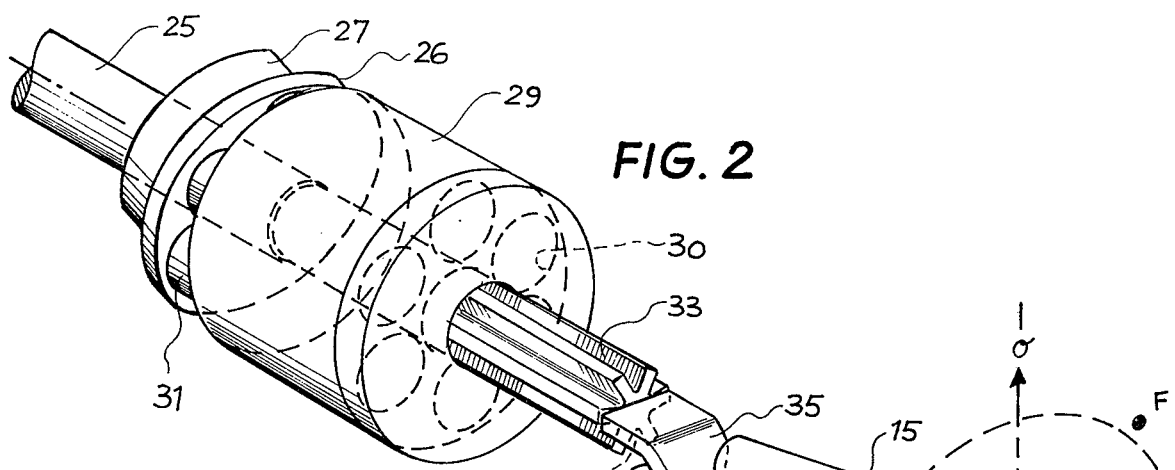
FIG. 2 is a pictorial view of the main operating parts of the device of FIG. 1 in the neutral position in which the rotor remains stationary.

The distributor member incorporates a bearing 24, in which one end of a drive shaft 25, is mounted. A swash plate 26, is mounted on a bearing 27, in a front plate 28, secured in the front end of the body 10. The swash plate is inclined to the axis of rotor 29, the angle of inclination being measured along an inclination diameter of the swash plate i.e. that diameter which produces the longest line when projected on the axis of rotor 29. As shown at FIG. 2, axis Ro and diameter $\sigma$ define a plane which passes through the inclination diameter of swash plate 26. Mounted on the shaft 25, is the rotor 29, having six longitudinal bores 30 as shown at FIG. 2 parallel to the axis of the shaft. In each bore is a piston 31, which is displaced by air pressure against the swash plate 28, to cause the shaft 25, to rotate.

The shaft 25, is supported at the front end by means of a bearing 32, mounted in the front plate 28.

The direction of rotation of the rotor is changed by varying the angular position of the distributor 18, in relation to the inclination diameter of the swash plate. The inlet and exhaust air 15 and 16, passes through passageways 33 and 34, six in all consisting of grooves in the shaft 25, in the region where the shaft 25 is mounted on bearing 24. The fronts ends of passageways 33 and 34 communicate with six radial passageways, in the rotor 29 only two of which are shown FIG. 1 and which each open in one of the piston bores 30. The distributor member is divided by a roughly diametrically extending baffle plate 35 the angular position of which determines the forward and reverse running of the rotor 29.

In FIG. 2 the air distribution member baffle 35, directs air to the grooves, and thus the pistons on both sides of the inclination diameter of the swash plate so that equal forces are exerted by these pistons and no movement of rotor 29 takes place. In this FIG. 2 position the axial portion of baffle 35 is perpendicular to diameter $\sigma$. Partial rotation of baffle 35 to the right, to the position of FIG. 3 directs more air to the bores 30 on the right side of diameter $\sigma$ and increases the forward speed of the rotor in a clockwise direction (as viewed from air inlet 15). Rotation of the baffle 35 to the FIG. 4 position, i.e. to the left from the position of FIG. 3, directs more air to the bores 30 on the left side of diameter $\sigma$ and causes reverse rotation of the rotor, i.e. counterclockwise as viewed from air inlet 15. Since distributor 18 is pinned to manifold 14, rotation of baffle 35 can readily be done by grasping body 10, and manifold 14, and rotating one with respect to the other. To avoid twisting of the hoses which will be connected to the air inlet 15 and outlet 16, body 10 will usually be turned with respect to manifold 14, thus rotating the inclination diameter of the swash plate with respect to baffle 35.

Figure 3:
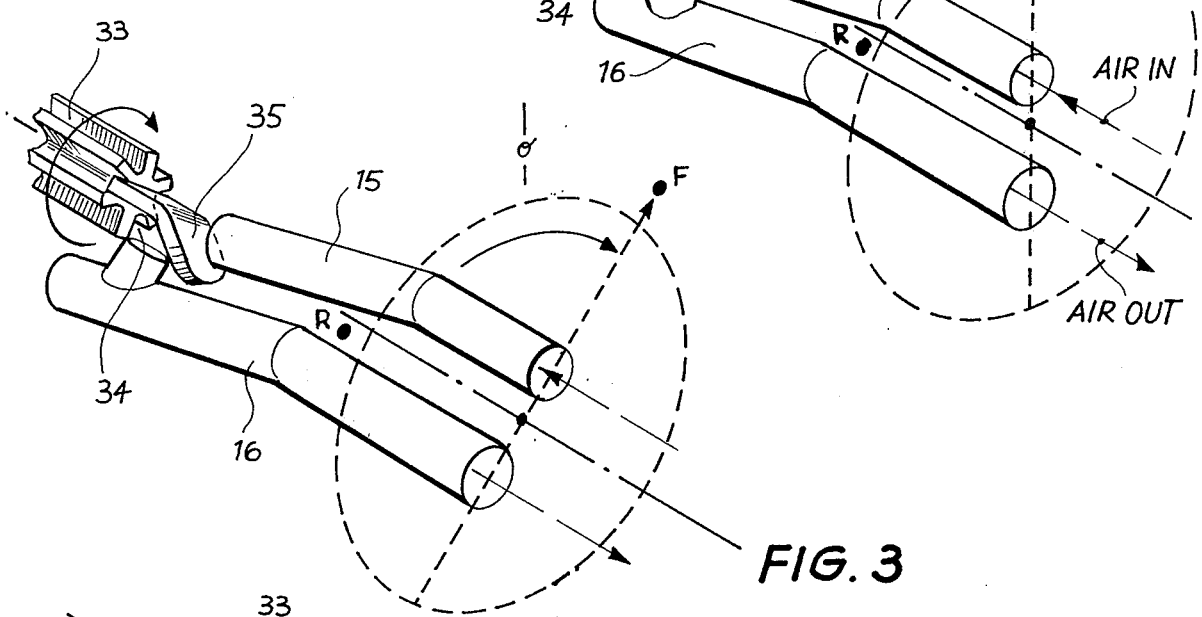
FIG. 3 is a pictorial view of the main operating parts of the device of FIG. 1 in the position to cause forward rotation of the rotor.

In FIG. 3 baffle 35 is turned clockwise to direct air from inlet 15 to the cylinders 30 on the right side of the inclination diameter of plate 26, and at the same time the cylinders on the left side of the inclination diameter communicate with exhaust 16. This causes forward or clockwise rotation of the rotor.

Figure 4:
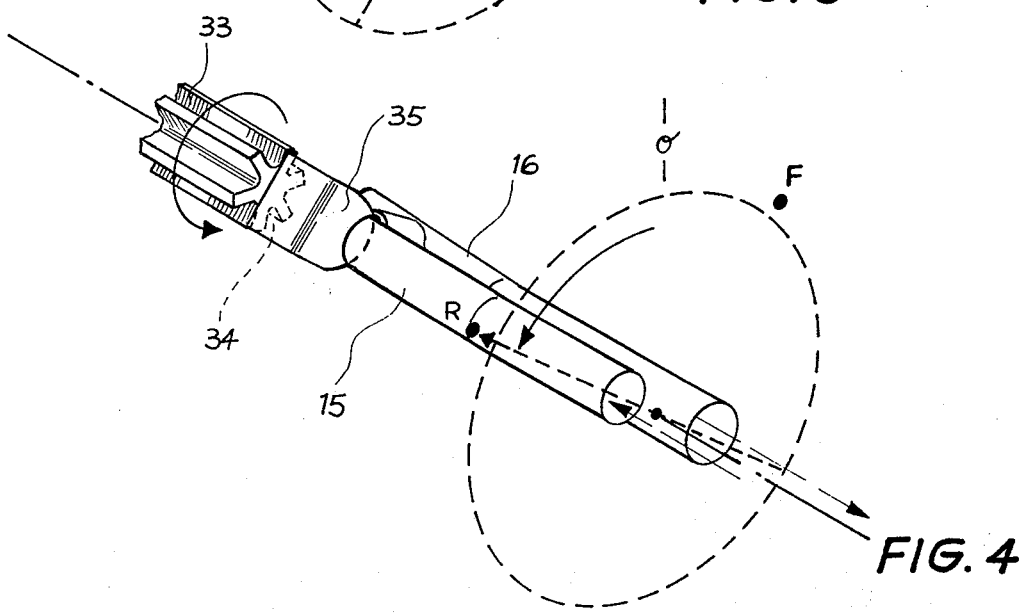
FIG. 4 is a pictorial view of the main operating parts of the device of FIG. 1 in the position to cause reverse rotation of the rotor.

In FIG. 4, baffle 35 is turned to the left from the position of FIG. 2 so inlet air from inlet 15 flows to the cylinders on the left of the inclination diameter of plate 26, and the cylinders on the right communicate with exhaust 16. This causes reverse or counterclockwise rotation of rotor 29.

In an intermediate position of baffle 35 between the positions of FIGS. 2 and 3, a majority of the air from the inlet will flow to the cylinders 30 on the right side of the inclination diameter of plate 26, but some air will flow to the pistons on the left side of this diameter. The pistons on the left side of the diameter will exert a slight restraining force to rotation of rotor 29 since, at such an intermediate position, the rotor will rotate clockwise but at a slower speed than when baffle 35 is in the FIG.

3 position. In this way, the speed of rotation of the rotor can be regulated by changing the angular position of baffle 35. Similarly, baffle 35 can be rotated to an intermediate position to the left, by rotating distributor 18 with respect to body 10 to control the speed of rotation of the rotor in a counterclockwise direction.

I claim:

1. A dental handpiece having a housing including a body member, an air distributing member mounted therein and in communication with a manifold member, a rotor member mounted on a shaft journalled with respect to the body member and having a plurality of bores in which pistons are axially slidable in response to air pressure, said pistons engaging the surface of a swash plate in the housing and of fixed inclination, and defining a fixed inclination diameter, with respect to the housing, the air distributing member being displaceable with respect to the body to vary the direction of inlet air and outlet air on either side of the inclination diameter of the plate, said air distributing member comprising means for selecting neutral, forward, and reverse rotation of the rotor, and any controlled speed between forward and reverse.

2. A dental handpiece as claimed in claim 1 in which the rotor member is mounted on a shaft and a brake member is mounted in the body, said brake member being displaced out of contact with the rotor when air pressure is applied to the rotor.

3. A dental handpiece as claimed in claim 1 in which the air distributing member is a plate member positioned in the path of air from an inlet and is arranged to direct air along passageways on the shaft.

4. A dental handpiece as claimed in claim 3 in which the plate member of the air distributing member is bent to deflect the air discharged by the pistons of the rotor into a discharge air pipe.

* * * * *